US 11,090,192 B2

(12) United States Patent
Sernfält

(10) Patent No.: US 11,090,192 B2
(45) Date of Patent: Aug. 17, 2021

(54) PERSONAL PROTECTIVE SYSTEM TOOL COMMUNICATION ADAPTER

(71) Applicant: 3M INNOVATIVE PROPERTIES COMPANY, St. Paul, MN (US)

(72) Inventor: Mats U. Sernfält, Leksand (SE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/966,105

(22) Filed: Apr. 30, 2018

(65) Prior Publication Data

US 2018/0243138 A1   Aug. 30, 2018

Related U.S. Application Data

(63) Continuation of application No. 15/502,071, filed as application No. PCT/US2015/049557 on Sep. 11, 2015, now Pat. No. 9,956,118.

(Continued)

(51) Int. Cl.

| A61F 9/06 | (2006.01) |
| G08C 17/02 | (2006.01) |
| F16P 3/00 | (2006.01) |

(52) U.S. Cl.
CPC .............. *A61F 9/064* (2013.01); *A61F 9/06* (2013.01); *A61F 9/061* (2013.01); *F16P 3/00* (2013.01); *G08C 17/02* (2013.01)

(58) Field of Classification Search
CPC .. A61F 9/061; A61F 9/064; F16P 3/00; G08C 17/02
See application file for complete search history.

(56) References Cited

U.S. PATENT DOCUMENTS

| 1,497,012 A | 6/1924 | Goodspeed |
| 1,822,308 A | 9/1931 | Norton |

(Continued)

FOREIGN PATENT DOCUMENTS

| AU | 7135615 | 11/1975 |
| CH | 224784 | 12/1942 |

(Continued)

OTHER PUBLICATIONS

Redoctobyr, "A way to pre-darken an auto-darkening helmet before the arc starts", [retrieved from internet on Mar. 10, 2017], URL <http://www.mytractorforum.com/showthread.php?t=227484>, 6 pages.

(Continued)

*Primary Examiner* — Yong Hang Jiang
(74) *Attorney, Agent, or Firm* — Gregg H. Rosenblatt

(57) ABSTRACT

A tool communication adapter system is provided. One exemplary system described herein includes a tool communication adapter having an adapter body including first and second mechanical attachment ends, a first electrical connector proximate the first mechanical attachment end and a second electrical connector proximate the second mechanical attachment end, a first supply channel having an opening extending through the body between the first and second mechanical attachment ends, and including a first supply channel connector at the first attachment end and a second supply channel connector at the second mechanical attachment end, and a control unit in communication with the first and second electrical connectors. The control unit is configured to provide a filter command signal to a protective filter in response to a signal received at the first electrical connector. An exemplary tool communication adapter thus allows communication between a tool and personal protective equipment.

16 Claims, 3 Drawing Sheets

Related U.S. Application Data

(60) Provisional application No. 62/050,342, filed on Sep. 15, 2014.

(56) References Cited

U.S. PATENT DOCUMENTS

| | | |
|---|---|---|
| 2,171,052 A | 8/1939 | Tatter |
| 2,417,883 A | 3/1947 | Oschin |
| 2,423,320 A | 7/1947 | Hurley |
| 2,471,719 A | 5/1949 | Broffitt |
| 2,514,990 A | 7/1950 | Dewan |
| 2,548,230 A | 4/1951 | Molyneux |
| 2,582,860 A | 1/1952 | Clerke |
| 2,678,369 A | 5/1954 | Van Hook |
| 2,761,046 A | 8/1956 | Herrick |
| 2,904,669 A | 9/1959 | Toebe |
| 3,096,430 A | 7/1963 | Farr |
| 3,137,784 A | 6/1964 | Kasemann |
| 3,159,844 A | 12/1964 | Haboush |
| 3,227,866 A | 1/1966 | Peters |
| 3,245,315 A | 4/1966 | Marks |
| 3,368,220 A | 2/1968 | Wenzel |
| 3,575,491 A | 4/1971 | Heilmeier |
| 3,719,793 A | 3/1973 | Finger |
| 3,731,986 A | 5/1973 | Fergason |
| 3,838,247 A | 9/1974 | Finger |
| 3,873,804 A | 3/1975 | Gordon |
| 3,881,808 A | 5/1975 | Gurtler |
| 3,890,628 A | 6/1975 | Gurtler |
| 3,902,169 A | 8/1975 | Washizuka |
| 3,918,796 A | 11/1975 | Fergason |
| 3,967,881 A | 7/1976 | Moriyama |
| 4,011,594 A | 3/1977 | Guilbaud |
| 4,039,254 A | 8/1977 | Harsch |
| 4,039,803 A | 8/1977 | Harsch |
| 4,052,209 A | 10/1977 | Huffman |
| 4,071,912 A | 2/1978 | Budmiger |
| RE29,684 E | 6/1978 | Gordon |
| 4,093,832 A | 6/1978 | Isaacson |
| 4,109,114 A | 8/1978 | Baer |
| 4,109,132 A | 8/1978 | Butoi |
| 4,143,264 A | 3/1979 | Gilbert |
| 4,155,122 A | 5/1979 | Budmiger |
| 4,237,557 A | 12/1980 | Gordon |
| 4,240,709 A | 12/1980 | Hornell |
| 4,241,286 A | 12/1980 | Gordon |
| 4,279,474 A | 7/1981 | Belgorod |
| 4,293,757 A | 10/1981 | Niemi |
| 4,328,493 A | 5/1982 | Shanks |
| 4,385,806 A | 5/1983 | Fergason |
| 4,418,267 A | 11/1983 | pfanzelt |
| 4,422,185 A | 12/1983 | Cook |
| 4,436,376 A | 3/1984 | Fergason |
| 4,540,243 A | 9/1985 | Fergason |
| 4,556,289 A | 12/1985 | Fergason |
| 4,560,239 A | 12/1985 | Katz |
| 4,638,146 A | 1/1987 | Koyama |
| 4,664,479 A | 5/1987 | Hiroshi |
| 4,679,254 A | 7/1987 | Wiegel |
| 4,679,255 A | 7/1987 | Kuhlman |
| 4,686,711 A | 8/1987 | Budmiger |
| 4,694,141 A | 9/1987 | Hahn |
| RE32,521 E | 10/1987 | Fergason |
| 4,710,694 A | 12/1987 | Sutphin |
| 4,719,340 A | 1/1988 | Palfi |
| 4,728,173 A | 3/1988 | Toth |
| 4,759,608 A | 7/1988 | Yang |
| 4,777,667 A | 10/1988 | Patterson |
| 4,821,292 A | 4/1989 | Childress |
| 4,844,569 A | 7/1989 | Wada |
| 4,853,973 A | 8/1989 | Boochard |
| 4,863,244 A | 9/1989 | Fuerthbauer |
| 4,875,235 A | 10/1989 | Kuhlman |
| 4,896,947 A | 1/1990 | Leenhouts |
| 4,920,257 A | 4/1990 | Fuerthbauer |
| 4,937,879 A | 7/1990 | Hall |
| 4,945,572 A | 8/1990 | Rosen |
| 4,952,030 A | 8/1990 | Nakagawa |
| 5,015,086 A | 5/1991 | Okaue |
| 5,074,647 A | 12/1991 | Fergason |
| 5,113,270 A | 5/1992 | Fergason |
| 5,140,707 A | 8/1992 | Johnson |
| 5,184,156 A | 2/1993 | Black |
| 5,189,735 A | 3/1993 | Corona |
| 5,191,468 A | 3/1993 | Mases |
| 5,208,688 A | 5/1993 | Fergason |
| 5,248,880 A | 9/1993 | Fergason |
| 5,252,817 A | 10/1993 | Fergason |
| 5,515,186 A | 5/1996 | Fergason |
| 5,533,206 A | 7/1996 | Petrie |
| 5,561,290 A * | 10/1996 | Strobel ............. G01J 1/02 250/252.1 |
| 5,666,010 A | 9/1997 | Stratiotis |
| 5,751,258 A | 5/1998 | Fergason |
| 5,825,441 A | 10/1998 | Hornell |
| 6,097,451 A | 8/2000 | Palmer |
| 6,168,278 B1 * | 1/2001 | Mukai ............. A61F 9/022 351/158 |
| 6,185,736 B1 | 2/2001 | Ueno |
| 6,185,739 B1 | 2/2001 | Verkic |
| 6,352,383 B1 | 3/2002 | Ristola |
| 6,395,104 B1 | 5/2002 | Kosuge |
| 6,507,954 B1 | 1/2003 | Sanchez |
| 6,635,125 B2 | 10/2003 | Kosuge |
| 6,734,393 B1 | 5/2004 | Friedl |
| 6,936,789 B2 | 8/2005 | Hanzel |
| 6,973,672 B2 | 12/2005 | Huh |
| D517,744 S | 3/2006 | Lee |
| D517,745 S | 3/2006 | Lee |
| D518,923 S | 4/2006 | Curran |
| 7,026,593 B2 | 4/2006 | Hamilton |
| D523,728 S | 6/2006 | Lee |
| 7,061,462 B1 | 6/2006 | Pirs |
| D532,163 S | 11/2006 | Curran |
| 7,193,767 B1 | 3/2007 | Peeri |
| 7,197,774 B2 | 4/2007 | Curran |
| 7,342,210 B2 | 3/2008 | Fergason |
| 7,477,330 B2 | 1/2009 | Magnusson |
| 7,637,622 B2 | 12/2009 | Garbergs |
| 7,810,937 B2 | 10/2010 | Garbergs |
| 8,042,958 B2 * | 10/2011 | Sundell ............. A61F 9/067 359/601 |
| 8,047,664 B2 | 11/2011 | Garbergs |
| 8,264,265 B2 | 9/2012 | Greiner |
| 8,339,822 B2 | 12/2012 | Klopcic |
| 8,599,323 B2 | 12/2013 | Chen |
| 8,626,087 B2 | 1/2014 | Vanderaa |
| 9,956,118 B2 | 5/2018 | Sernfalt |
| 2004/0190106 A1 * | 9/2004 | McLear ............. A61F 9/022 359/276 |
| 2005/0009695 A1 | 1/2005 | Klumpe |
| 2006/0101552 A1 | 5/2006 | Lee |
| 2006/0107431 A1 | 5/2006 | Curran |
| 2007/0056072 A1 | 3/2007 | Steinemann |
| 2007/0056073 A1 | 3/2007 | Martin |
| 2007/0080621 A1 | 4/2007 | Huh |
| 2007/0081250 A1 | 4/2007 | Garbergs |
| 2008/0280568 A1 | 11/2008 | Kielb |
| 2010/0089887 A1 | 4/2010 | Friedl |
| 2010/0132086 A1 | 6/2010 | Huh |
| 2011/0248012 A1 | 10/2011 | Fujiwara |
| 2011/0251838 A1 | 10/2011 | Huh |
| 2014/0013479 A1 * | 1/2014 | Magnusson ............. A61F 9/067 2/8.7 |
| 2014/0097778 A1 * | 4/2014 | Yeh ............. G08C 17/02 318/434 |
| 2017/0255027 A1 * | 9/2017 | Hofer-Kraner ........ G02C 5/122 |
| 2017/0368381 A1 * | 12/2017 | Awiszus ............. A62B 9/006 |
| 2019/0175411 A1 * | 6/2019 | Awiszus ............. A62B 9/006 |

FOREIGN PATENT DOCUMENTS

| | | |
|---|---|---|
| CN | 201710541 | 1/2011 |
| DE | 2742211 | 3/1979 |

(56) References Cited

FOREIGN PATENT DOCUMENTS

| | | |
|---|---|---|
| DE | 3503958 | 8/1986 |
| DE | 3524929 | 1/1987 |
| DE | 3700423 | 7/1987 |
| DE | 8806151 | 6/1988 |
| DE | 3729964 | 3/1989 |
| DE | 3842824 | 6/1990 |
| EP | 0005417 | 11/1979 |
| EP | 0189231 | 7/1986 |
| EP | 0157744 | 5/1989 |
| EP | 0349665 | 1/1990 |
| EP | 0926250 | 6/1999 |
| EP | 1459715 | 9/2004 |
| EP | 2279824 | 2/2011 |
| EP | 2338446 | 6/2011 |
| FR | 1314901 | 1/1963 |
| FR | 2530039 | 1/1984 |
| FR | 2532575 | 3/1984 |
| FR | 2560824 | 9/1985 |
| GB | 325586 | 2/1930 |
| GB | 482953 | 4/1938 |
| GB | 565800 | 3/1944 |
| GB | 731363 | 6/1955 |
| GB | 878847 | 10/1961 |
| GB | 929594 | 6/1963 |
| GB | 935467 | 8/1963 |
| GB | 959413 | 6/1964 |
| GB | 982350 | 2/1965 |
| GB | 1077096 | 7/1967 |
| GB | 1430183 | 3/1976 |
| GB | 1450915 | 9/1976 |
| GB | 2034171 | 6/1980 |
| GB | 2065909 | 7/1981 |
| GB | 2077167 | 12/1981 |
| GB | 2139373 | 11/1984 |
| GB | 2196145 | 4/1988 |
| GB | 2208323 | 3/1989 |
| JP | 55-92276 | 7/1980 |
| JP | 59-035624 | 2/1984 |
| JP | 59-226115 | 12/1984 |
| JP | 60-33142 | 2/1985 |
| JP | 60-121222 | 6/1985 |
| JP | 61-12823 | 1/1986 |
| JP | 64-62417 | 3/1989 |
| JP | 02-274813 | 11/1990 |
| RU | 2181213 | 4/2002 |
| RU | 2248022 | 3/2005 |
| SU | 1586704 | 8/1990 |
| SU | 1586705 | 8/1990 |
| WO | WO 1984/01037 | 3/1984 |
| WO | WO 1988/05926 | 8/1988 |
| WO | WO 1988/06030 | 8/1988 |
| WO | WO 1990/14611 | 11/1990 |
| WO | WO 1990/14809 | 12/1990 |
| WO | WO 1995/29428 | 11/1995 |
| WO | WO 1997/15255 | 5/1997 |
| WO | WO 2004/053586 | 6/2004 |
| WO | WO 2004/102265 | 11/2004 |
| WO | WO 2005/102230 | 11/2005 |
| WO | WO 2006/010230 | 2/2006 |
| WO | WO 2007/025315 | 3/2007 |
| WO | WO 2007/047264 | 4/2007 |
| WO | WO 2008/037304 | 4/2008 |
| WO | WO 2011/000074 | 1/2011 |

OTHER PUBLICATIONS

International Search Report for PCT International Application No. PCT/US2015/049557, dated Dec. 2, 2015, 4 pages.

* cited by examiner

PERSONAL PROTECTIVE SYSTEM TOOL COMMUNICATION ADAPTER

TECHNICAL FIELD

The present description is directed to a communication adapter for a tool, particular a communication adapter that provides communication between a tool and a personal protective device.

BACKGROUND

Protective filters are often used to protect users from intense levels of incident light, such as the glare of a welding arc, for example, and have been incorporated in various eyewear, masks, helmets, or other head gear. Automatic darkening filters generally include control circuitry which causes the filter to change from a light state when not subjected to glare and to a dark state upon exposure to such glare. Passive filters generally include a permanently dark filter that may be moved into and out of a position of use over a user's eyes as desired.

Various mechanisms have been provided for automatically shielding a user from a glare of a welding arc or other tool. For example, automatic darkening filters have been provided which darken in response to activation of a tool. Passive filters have been provided that move a protective filter in response to an input of a user or initiation of a welding tool. For example, U.S. Pat. No. 8,047,664 describes a protective automatic darkening filter (ADF) and an associated tool, such as a welding torch, that are controlled by a corresponding communication unit such that the tool is not activated before the ADF has reached its dark state. GB 2034171 describes a filter movable into alignment with a window before a welding arc can be struck and a mechanism involving a solenoid operated device is incorporated into the helmet to actuate movement of the filter. In order to prevent the striking of an arc until the filter is in place, a switch is incorporated which is only operated when the filter is in position and electrical connections between the switch and an electrical control circuit prevent the flow of arc current to a welding tool until the switch has been closed.

SUMMARY

The present description provides tool communication adapter system, including a tool communication adapter that may be incorporated with a tool to provide communication between the tool and personal protective equipment. In an exemplary embodiment, a tool communication adapter is provided including an adapter body having first and second mechanical attachment ends, a first electrical connector proximate the first mechanical attachment end and a second electrical connector proximate the second mechanical attachment end, a first supply channel having an opening extending through the body between the first and second mechanical attachment ends, and a first supply channel connector at the first attachment end and a second supply channel connector at the second mechanical attachment end, and a control unit in communication with the first and second electrical connectors. The control unit is configured to provide a filter command signal to a protective filter in response to a signal received at the first electrical connector.

In another exemplary embodiment, a system is providing including a tool having a user input configured to generate a tool activation signal, a tool power controller configured to provide power to the tool in response to the user input, and a communication adapter attachable between the tool and the tool power controller. The tool communication adapter including a body having first and second mechanical attachment ends and first and second electrical connectors proximate the first and second mechanical attachment ends, a wire channel extending through the body between the first and second mechanical attachment ends and having a first wire channel connector at the first attachment end and a second wire channel connector at the second mechanical attachment end, a gas supply tube extending through the body between the first and second mechanical attachment ends having a first gas supply tube connector at the first attachment end and a second gas supply tube connector at the second mechanical attachment end, and a control unit in communication with the first and second electrical connectors. The exemplary system further includes a protective filter movable between a closed position and an open position in response to a filter command signal. The control unit is configured to provide a closed filter command signal to the protective filter in response to the tool activation signal.

The above summary is not intended to describe each disclosed embodiment or every implementation. The Figures and Detailed Description, which follow, more particularly exemplify illustrative embodiments.

BRIEF DESCRIPTION OF DRAWINGS

The disclosure may be further explained with reference to the appended Figures, wherein like structure is referred to by like numerals throughout the several views, and wherein.

Figure 1A:
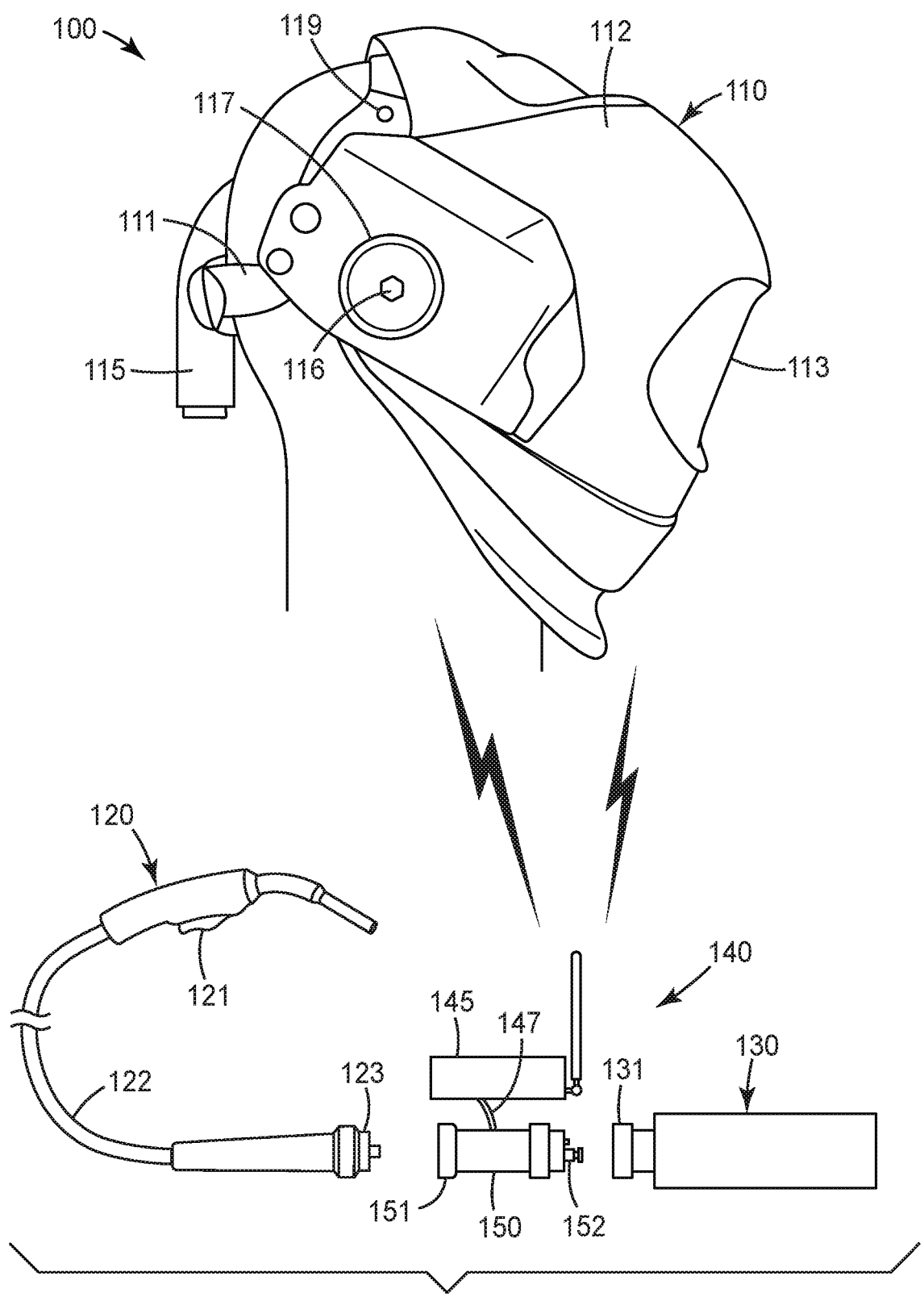
FIG. 1a is a schematic view of an exemplary system including a tool communication adapter according to the present description and an exemplary protective filter in a closed position.

While the above-identified figures set forth various embodiments of the disclosed subject matter, other embodiments are also contemplated. In all cases, this disclosure presents the disclosed subject matter by way of representation and not limitation. It should be understood that numerous other modifications and embodiments can be devised by those skilled in the art which fall within the scope and spirit of the principles of this disclosure.

DETAILED DESCRIPTION

The present description provides a tool communication adapter and system. The tool communication adapter includes a control unit that allows control of a tool and a protective filter. The tool communication adapter is configured to be attached between a tool and tool power controller, for example, to allow communication with a protective filter. The protective filter is instructed to a closed position to protect a user's eyes, and face, for example, in response to a command signal provided by the control unit before the tool may be activated. In this way, a system, such as a welding system, may be adapted to communicate with a protective filter to ensure a darkened protective filter is in position to protect a user's eyes and/or face before the tool is activated.

FIG. 1 shows an exemplary system 100 including a headgear 110 having a protective filter 113, a tool 120, a power controller 130, and a tool communication adapter 140. In an exemplary embodiment, tool communication adapter 140 is connectable between tool 120 and power controller 130, and is configured to communicate with protective filter 113, tool 120, and/or power controller 130.

Tool 120 may include a welding tool, such as a metal inert gas (MIG) welding torch or metal active gas (MAG) welding torch, or other power or machine tool. In various exemplary embodiments, tool 120 includes a user input 121, and may include one or more other components including a cable 122 and a tool connector 123, for example. Power controller 130 includes power control electronics to provide energy to tool 120, and includes a power controller connector 131 having features complementary and attachable to tool connector 123. In an exemplary embodiment, tool connector 123 may be directly connected to power controller connector 131 such that power controller 130 provides power to tool 120 in response to activation of user input 121.

User input 121 of tool 120 may be activated by a user to generate a tool activation signal to control the start and stop of tool 120, or adjust other parameters of tool 120. For example, in a welding application, pressing or releasing one or more user inputs 121 of tool 120 controls the start and stop of a welding arc generated by tool 120, and/or the passage of consumable materials, such as wire and gas, through tool 120. In various exemplary embodiments, user input 121 may be a switch, knob, dial, touch sensor, or other suitable input mechanism, generating a tool activation signal by completing a circuit, for example, that allows power to be supplied from power controller 130 to tool 120.

Figure 1B:
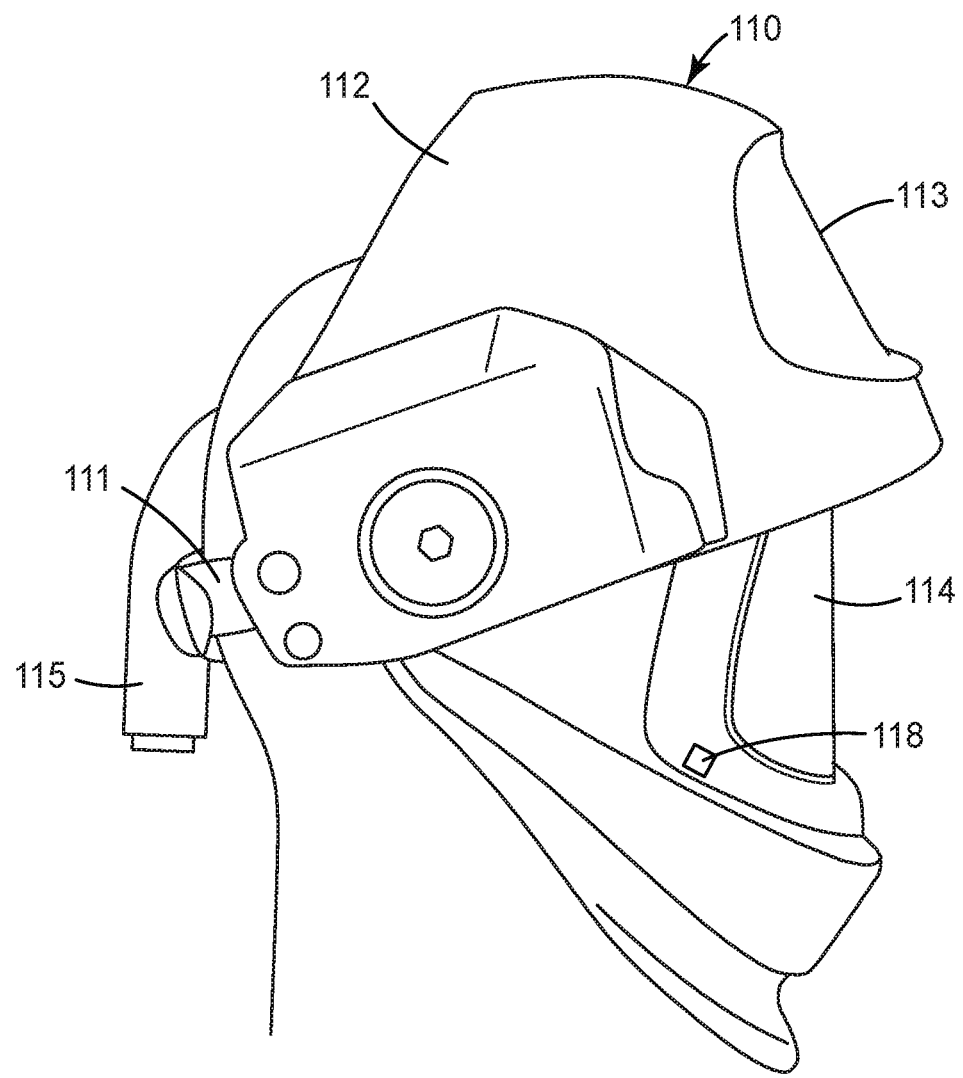
FIG. 1b is a schematic view of an exemplary protective filter in an open position.

In an exemplary embodiment, headgear 110 includes at least one strap 111, a headgear body or frame 112, a protective filter 113, and a shield 114 (FIG. 1b). Shield 114 is positioned on body 112 such that shield 114 is generally in front of a user's eyes when the helmet is worn in a normal position of use, and may be fixed or movably attached to body 112. In an exemplary embodiment, shield 114 is curved to provide a wide viewing area and is relatively more transparent than protective filter 113. Protective filter 113 is movably mounted to body 112 such that protective filter 113 may be moved between a closed position to offer desired protection for a user, and an open position (FIG. 1b) in which a user may view surroundings substantially through shield 114. In various exemplary embodiments, headgear 110 may include a source of breathable air, such as hose 115, and may include a face seal to separate a breathing zone within the helmet, proximate a user's nose and mouth for example, from the ambient air.

Protective filter 113 is configured to move between a closed position shown in FIG. 1a and an open position shown in FIG. 1b. In an exemplary embodiment, protective filter 113 pivots or rotates at an attachment location 116 by an actuator 117. Actuator 117 may be a motor, solenoid, or other suitable actuator capable of moving protective filter 113 between a closed position and an open position. In an exemplary embodiment, actuator 117, for example, is joined to body 112 of headgear 110 to move protective filter 113. In an exemplary embodiment, protective filter includes a power supply, such as a battery, capacitor, solar cell, other suitable power supplies, and/or combinations thereof, configured to provide power to actuator 117 in response to a command message.

In various exemplary embodiments, protective filter 113 includes one or more sensors 118. Sensors 118 are located to detect a position of protective filter 113, such as, for example, whether protective filter 113 is in a closed position or an open position. In an exemplary embodiment, sensor 118 is located proximate protective filter 113 and detects protective filter 113 in a closed or open position. In other exemplary embodiments, sensor 118 is associated with actuator 117 and detects a position of actuator 117 corresponding to an open or closed position of protective filter 113. In an exemplary embodiment, sensor 118 is an inductive switch. Other suitable sensors 118 include capacitive switches, reflective switches, photointerrupters, microswitches, other suitable sensors, and/or combinations thereof as may be known in the art.

In an exemplary embodiment, protective filter 113 communicates an open return signal to control unit 145 when in an open position and/or a closed return signal when in a closed position, in response to a command signal received from control unit 145, for example, as described further herein.

In an exemplary embodiment, headgear 110 and/or protective filter 113 includes one or more sensors 119 positioned to detect whether headgear 110 is positioned on a user's head or over a user's eyes. Control unit 145 may require a signal indicating a user is detected by sensor 119 before allowing activation of tool 120 to ensure headgear 110 is positioned on a user.

Figure 2A:
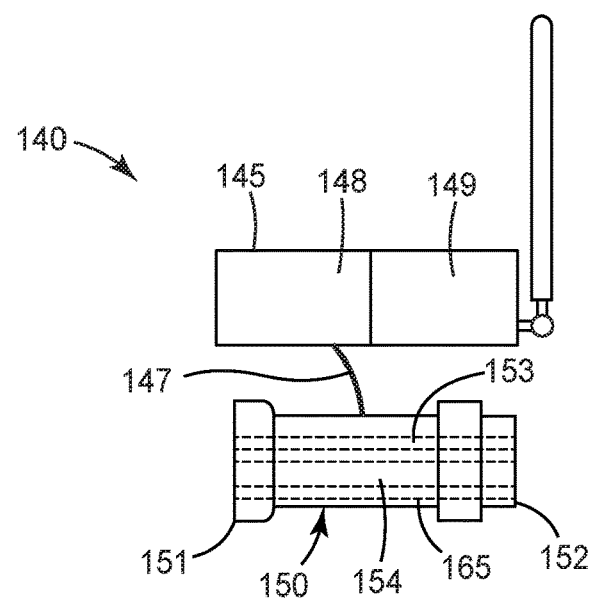
FIGS. 2a through 2c are schematic views of an exemplary tool communication adapter according to the present description.
Figure 2B:
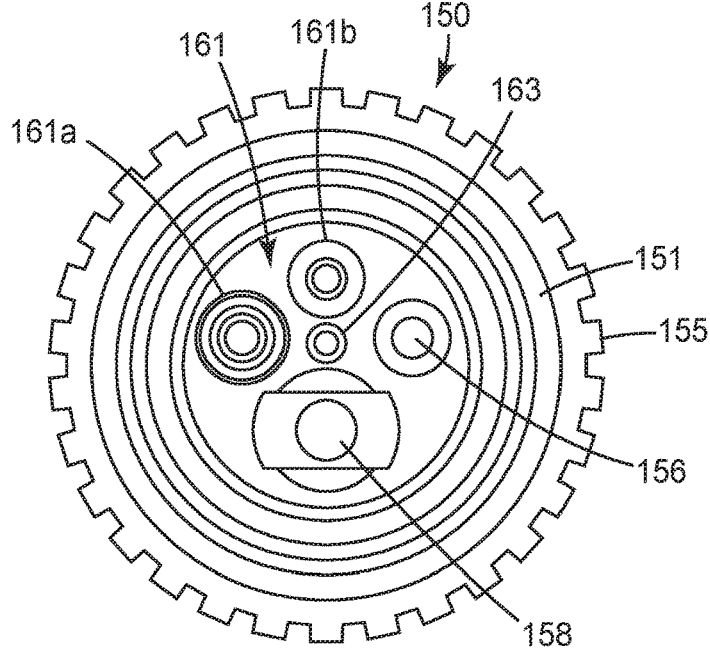
Figure 2C:
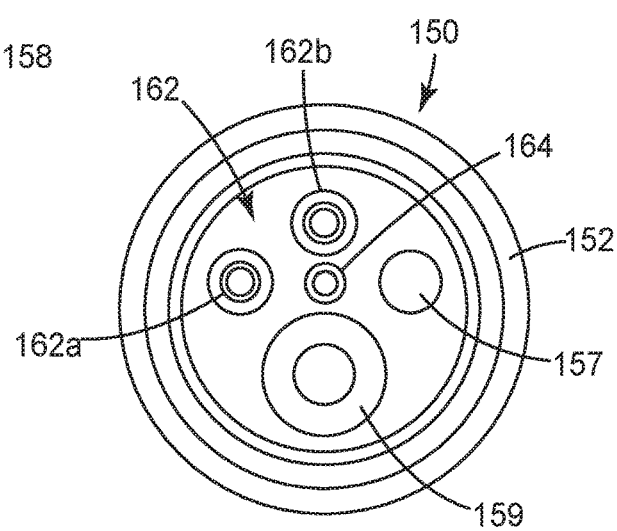

FIGS. 2a through 2c show exemplary tool communication adapter 140 configured to connect a tool and power controller, for example, such as tool 120 and power controller 130. In an exemplary embodiment, tool communication adapter 140 may be connected between tool 120 and power controller 130 to add communication capability to an existing tool system, particularly communication with a protective filter worn by a user and remote from a tool and power controller (e.g. not wired or physically connected to a tool or power controller).

Tool communication adapter 140 is positioned between tool 120 and power controller 130 and is configured to provide a command signal to protective filter 113. In an exemplary embodiment, control unit 145 of tool communication adapter 140 is configured to generate a closed command signal instructing protective filter 113 to move to a closed position and an open command signal to move to an open position, in response to a tool activation signal generated by tool 120.

Tool communication adapter 140 includes a body 150 including first and second mechanical attachment ends 151, 152, a supply channel 153, and a control unit 145. Supply channel 153 provides a passageway or opening for a material to pass through body 150 of tool communication adapter 140 and includes first and second supply channel connectors 156, 157 at the first and second mechanical attachment ends 151, 152. For example, supply channel 153 may allow the passage of consumable materials, such as a welding wire or a shielding gas of a welding operation. In an exemplary embodiment, tool communication adapter 140 includes a first supply channel providing a gas supply tube 153 and a second supply channel providing a wire channel 154. Gas supply tube 153 and wire channel 154 extend between first and second mechanical attachment ends 151, 152 and include, respectively, a first gas supply tube connector 156 and a first wire channel connector 158 at the first attachment end 151 and a second gas supply tube connector 157 and a second wire channel connector 159 at the second mechanical attachment end 152. First and second mechanical attachment ends are configured to attach to tool 120 and/or power controller 130. First and second gas supply tube connectors 156, 157 and first and second wire channel connectors 158, 159 are configured to connect to complementary features of tool 120 and/or power controller 130 such that wire and gas provided by power controller 130 may pass from power controller 130, through tool communication adapter 140, to tool 120.

First and second mechanical attachment ends 151, 152 provide a secure connection with tool connector 123 and power controller connector 131. In an exemplary embodiment, first and second mechanical attachment ends 151, 152 include a threaded fastener to tighten and secure a connection after wire channel connectors, gas supply tube connectors, electrical connectors, and/or other connectors are joined, or plugged together, with tool connector 123 or power controller connector 131. In other exemplary embodiments, connectors providing a secure attachment may be used, including, a flanged end connector, snap-fit connector, bayonet connector, other suitable mechanisms as known in the art, and/or combinations thereof.

Tool communication adapter 140 further comprises control unit 145 electrically positioned between first and second electrical connectors 161, 162, of tool communication adapter body 150. In various exemplary embodiments, first and second electrical connectors 161, 162 may include one, two or more electrical terminals 161*a*, 161*b*, and 162*a*, 162*b*, respectively, for example. When tool communication adapter 140 is attached to tool connector 123, control unit 145 is operatively connected to user input 121 of tool 120 such that control unit 145 may detect a tool activation signal generated by tool 120. Control unit 145 is configured to generate a command signal directed to a protective filter in response to the tool activation signal, as described further herein. Control unit 145 is further configured to selectively connect a circuit between first and second electrical connectors 161, 162. In an exemplary embodiment, connection of a circuit between first and second electrical connectors 161, 162 allows tool activation signal to be detected by power controller 130 such that power controller 130 may provide power to tool 120. Alternatively or in addition, connection of a circuit between first and second electrical connectors 161, 162 may allow electrical power and/or control information to be provided from power controller to tool 120 or tool communication adapter 140.

In an exemplary embodiment, an electrical circuit between first and second electrical connectors 161, 162 transmits a signal, for example a tool activation signal, and an electrical conductor 165 transmits power through tool communication adapter. For example, electrical conductor 165 allows passage of power through tool communication adapter 140 from a power controller to a tool. In various exemplary embodiments, electrical conductor 165 may be provided by body 150 of tool communication adapter 145 that is made of an appropriate electrically conductive material. Body 150 may include an electrically insulating coating or covering 155, such as a plastic material. In another exemplary embodiment, electrical conductor 165 is a metal wire conductor extending between third and fourth electrical connectors 163, 164.

In an exemplary embodiment, control unit 145 includes an input component such as a microcontroller 148. Microcontroller 148 detects a tool activation signal and generates a command signal that may be provided to a protective filter in response to the tool activation signal. In an exemplary embodiment, after receiving an appropriate signal, such as a closed return signal from a protective filter, microcontroller 148 causes an electrical circuit between first and second electrical connectors 161, 162 to be closed such that tool activation signal may be transmitted through tool communication adapter 140 to a power controller, for example. A relay 149, or other suitable switch or component causes the electrical circuit to be closed.

In an exemplary embodiment, control unit 145 is positioned within body 150 such that control unit 145, gas supply tube 153, and wire channel 154 are within a common housing. In other exemplary embodiments, control unit 145 may be joined to body 150 or provided in a separate housing connected to body 150 by one or more wires 147.

In various exemplary embodiments, tool communication adapter 140 communicates additional information between protective filter 113, tool 120, and/or power controller 130. For example, tool communication adapter 140 may be configured to communicate with only one particular protective filter 113 and/or one tool 120, and thus may provide unique identity codes within the command signals or return signals. A unique association prevents undesired communication with nearby protective filters or tools, as well as minimizes possible interference from surrounding sources of electricity or magnetic fields.

Tool communication adapter 140 may communicate wirelessly or via a wired connection. In an exemplary embodiment, control unit 145 of tool communication adapter 140 communicates wirelessly with protective filter 113 using a BLUETOOTH communication protocol. In other exemplary embodiments, control unit 145 communicates using infrared, radio-frequency, or acoustical communication, and/or any suitable protocol including BLUETOOTH, ZIGBEE, or other suitable protocol. In an exemplary embodiment, control unit 145 is configured to communicate with protective filter over a short distance, for example between 1 m and 30 m, 2 m and 20 m, or about 5 m. A small distance minimizes energy usage required by control unit 145 while also minimizing unwanted interference by devices that may be used simultaneously in the vicinity.

In an exemplary embodiment, tool communication adapter 140 includes a power source that supplies sufficient power to control unit 145 to generate command signals and/or perform other tasks. Power source may include a battery, solar cell, or other suitable power source. In some exemplary embodiments, tool communication adapter 140 is powered by electrical energy received from power controller 130. As described above, power controller 130 delivers sufficient power for operation of tool 120. A portion of the power delivered by power controller 130 may be harvested to power control unit 145 of tool communication adapter 140. In some exemplary embodiments, power received by control unit 145 from power controller 130 is sufficient such that tool communication adapter 140 does not include an independent or additional power source. For example, an exemplary tool communication adapter 140 includes a coil, such as an inductive coil, magnetically coupled to conductor 165 of tool communication adapter 140. The coil converts fluctuations in welding current to electrical power for control unit 145. Alternatively or in addition, a voltage drop across the current conductor and/or adapter body 150 may be used as a source of power for control unit 150.

In an exemplary embodiment, communication between tool communication adapter 140, protective filter 113, tool 120, and/or power controller 130 is initiated when tool communication adapter 140 receives a tool activation signal. Tool activation signal may be generated by a user input 121 of tool 120 (FIG. 1), as described above for example, and may result from an electrical connection closed or opened by user input 121. Tool activation signal may be any suitable digital or analog signal detected by tool communication adapter 140.

One or more additional inputs may be required for communication tool adapter to allow tool 120 to be activated and powered by power controller 130. In an exemplary embodiment, a user input on headgear 110, tool communication adapter 140, power controller 130, or a sensor 118 detecting positioning of headgear 110 on a user, or other suitable input, for example is required to initiate communication.

After receiving a tool activation signal to activate tool 120, tool communication adapter 140 generates a closed command signal communicated to protective filter 113 by control unit 145. Closed command signal instructs protective filter 113 to move to a closed position and may provide other additional information such as a unique identity code. Protective filter 113 is configured to generate and communicate a return signal to control unit 145. When control unit 145 receives a closed return signal, control unit 145 electrically connects first and second electrical connectors 161, 162 such that tool activation signal may be received by power controller 130. Power controller 130 provides power and/or other electrical signals to activate tool 120. In this way, tool communication adapter 140 ensures that protective filter is in a desired position before tool 120 may receive power from power controller 130.

When a tool deactivation signal, for example by pressing or releasing user input 121 of tool 120, is received by control unit 145 of tool communication adapter 140, first and second electrical connectors 161, 162 are electrically disconnected such that power is no longer delivered from power controller 130 to tool 120. Control unit 145 provides an open command signal to protective filter 113 instructing protective filter 113 to move to an open position. In some exemplary embodiments, an open return signal is communicated to control unit 145.

A tool communication adapter as described herein provides several features and advantages. An exemplary tool communication adapter may be used with existing tools and/or power controllers to adapt an existing system to allow communication between one or more components and a protective filter. The tool communication adapter thus provides additional safety advantages by preventing operation of a tool before a protective filter is in an appropriate position, and does not rely on sensing a welding arc or other source of light from which a user is to be protected. A tool communication adapter as described herein thus provides highly reliable control of a protective filter, tool and/or power controller.

When used with a protective filter having an actuator, protective filter automatically moves into an appropriate position without additional manipulation by the user. Accordingly, tool communication adapter allows a system to combine advantages of a passive protective filter, including a wide angle of view, immediate protection and a lighter or more transparent light state provided by an associated shield, with the ease of use and safety advantages of automatic positioning in response to activation of a tool. Further, automatic movement of a passive filter using a tool communication adapter as described herein allows a relatively slower transition between a dark state and a light state, minimizing discomfort that may be associated with rapid transition, while providing automatic protection.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the exact details and structures described herein, but rather by the structures described by the language of the claims, and the equivalents of those structures. Any patent literature cited herein is hereby incorporated herein by reference in its entirety to the extent that it does not conflict with the description presented herein.

Any feature or characteristic described with respect to any of the above embodiments can be incorporated individually or in combination with any other feature or characteristic, and are presented in the above order and combinations for clarity only. That is, the present disclosure contemplates all possible combinations and arrangements of various features of each of the exemplary embodiments and components describe herein, and each component may be combined or used in conjunction with any other component as may be desired for a particular application.

What is claimed is:

1. A system comprising:
   a welding tool comprising a user input configured to generate a tool activation signal;
   a tool power controller configured to provide power to the tool in response to the user input;
   a tool connector for connecting the welding tool to the tool power controller such that the tool power controller provides power to the tool in response to activation of the user input;
   welding headgear including a body and a shield positioned on the body, the shield having a wide viewing area configured to be positioned in front of a user's eyes during normal use, wherein the shield is configured to protect the user's eyes and face before the tool is activated;
   a protective filter movably mounted to the welding headgear configured to be worn by the user, wherein the protective filter is mounted to an attachment location on the headgear and physically moves in relation to the headgear between an open position away from the user's eyes and a closed position to cover the shield and user's eyes in response to a closed filter command signal, and wherein the protective filter moves back to an open position in response to an open command signal, wherein the protective filter rotates at the attachment location by an actuator, wherein the attachment location is disposed on a side region of the welding headgear body; and
   a control unit in communication with the tool connector; wherein the control unit is configured to provide the closed filter command signal to the protective filter in response to the tool activation signal,
   wherein the protective filter includes at least a first sensor located to detect a position of the protective filter and wherein at least one of the protective filter and the welding headgear includes a second sensor to detect whether the welding headgear is positioned on at least one of a user's head and over a user's eyes.

2. The system of claim 1, wherein the protective filter generates a closed return signal when moved to the closed position.

3. The system of claim 1, wherein the tool power controller is configured to supply power to the tool when the protective filter generates a closed signal.

4. The system of claim 1, wherein the protective filter generates an open return signal when moved to the open position.

5. The system of claim 1, wherein the user input further comprises a tool deactivation signal, and the control unit provides the open command signal to the protective filter in response to the tool deactivation signal.

6. The system of claim 1, wherein the control unit comprises a microcontroller configured to detect a tool activation signal.

7. The system of claim 1, wherein the first sensor is located to detect an open position or a closed position of the protective filter.

8. The system of claim 1, wherein the first sensor is located proximate the protective filter to detect an open position or a closed position of the protective filter.

9. The system of claim 1, wherein the first sensor is associated with the actuator capable of moving the protective filter between a closed position and an open position to detect a position of the actuator corresponding to an open position or a closed position of the protective filter.

10. The system of claim 1, wherein the first sensor includes at least one of an inductive switch, a capacitive switch, a reflective switch, a photointerrupter, and a microswitch.

11. A system comprising:
a welding tool comprising a user input configured to generate a tool activation signal;
a tool power controller configured to provide power to the welding tool in response to the user input;
a tool communication adapter attachable between the welding tool and the tool power controller such that the tool power controller provides power to the tool in response to activation of the user input, and comprising an adapter body having first and second mechanical attachment ends and first and second electrical connectors proximate the first and second mechanical attachment ends;
welding headgear including a body and a shield positioned on the body, the shield having a wide viewing area configured to be positioned in front of a user's eyes during normal use, wherein the shield is configured to protect the user's eyes and face before the tool is activated;
a protective filter movably mounted to the welding headgear configured to be worn by the user, wherein the protective filter is mounted to an attachment location on the headgear and physically moves in relation to the headgear between an open position away from the user's eyes and a closed position to cover the shield and user's eyes in response to a closed filter command signal, and wherein the protective filter moves back to an open position in response to an open command signal, wherein the protective filter rotates at the attachment location by an actuator, wherein the attachment location is disposed on a side region of the welding headgear body; and
a control unit in communication with the first and second electrical connectors and configured to selectively electrically connect the first and second electrical connectors,
wherein the first mechanical attachment end provides for direct mechanical attachment to a tool and the second mechanical attachment end provides for direct mechanical attachment to the tool power controller,
wherein the protective filter includes at least a first sensor located to detect a position of the protective filter and wherein at least one of the protective filter and the welding headgear includes a second sensor to detect whether the welding headgear is positioned on at least one of a user's head and over a user's eyes.

12. The system of claim 11, wherein the control unit is configured to provide the closed filter command signal to the protective filter in response to the tool activation signal.

13. The system of claim 11, wherein the control unit is configured to selectively electrically connect the first and second electrical connectors such that the tool power controller detects the tool activation signal to provide power to the tool.

14. The system of claim 11, wherein the control unit is configured to selectively electrically connect the first and second electrical connectors such that at least one of electrical power and control information is provided from the power controller to the tool or the tool communication adapter.

15. The system of claim 11, wherein the control unit is positioned within the adapter body, joined to the adapter body, or provided in a separate housing connected to the adapter body by one or more wires.

16. The system of claim 1, wherein the closed command signal provides a unique identifier code.

* * * * *